United States Patent
Bublitz et al.

(10) Patent No.: US 8,967,806 B2
(45) Date of Patent: Mar. 3, 2015

(54) FUNDUS CAMERA WITH STRIP-SHAPED PUPIL DIVISION, AND METHOD FOR RECORDING ARTIFACT-FREE, HIGH-RESOLUTION FUNDUS IMAGES

(75) Inventors: Daniel Bublitz, Rausdorf (DE); Lothar Müller, Ottendorf (DE); Uwe Mohrholz, Jena (DE); Thomas Mohr, Jena (DE); Frank Teige, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 13/883,237

(22) PCT Filed: Nov. 4, 2011

(86) PCT No.: PCT/EP2011/005558
§ 371 (c)(1),
(2), (4) Date: May 2, 2013

(87) PCT Pub. No.: WO2012/059236
PCT Pub. Date: May 10, 2012

(65) Prior Publication Data
US 2013/0222763 A1    Aug. 29, 2013

(30) Foreign Application Priority Data
Nov. 6, 2010   (DE) .......................... 10 2010 050 693

(51) Int. Cl.
*A61B 3/14*   (2006.01)
*A61B 3/00*   (2006.01)

(52) U.S. Cl.
USPC ......................................... 351/206; 351/246

(58) Field of Classification Search
USPC ................................................ 351/200–246
See application file for complete search history.

(56) References Cited

U.S. PATENT DOCUMENTS

| 4,170,398 | A |   | 10/1979 | Koester |
|---|---|---|---|---|
| 4,331,392 | A |   | 5/1982 | Sato |
| 4,732,466 | A |   | 3/1988 | Humphrey |
| 4,991,953 | A |   | 2/1991 | Pflibsen et al. |
| 5,713,047 | A | * | 1/1998 | Kohayakawa ................. 396/18 |
| 5,847,805 | A |   | 12/1998 | Kohayakawa et al. |
| 6,520,640 | B1 |   | 2/2003 | Binnun |
| 6,698,887 | B2 | * | 3/2004 | Eikelboom et al. ........... 351/221 |
| 7,481,535 | B2 | * | 1/2009 | Yancey et al. ................ 351/221 |

(Continued)

FOREIGN PATENT DOCUMENTS

| DE | 10 2005 032 501 A1 | 3/2006 |
|---|---|---|
| JP | 2007 151651 A | 6/2007 |

(Continued)

*Primary Examiner* — Mohammed Hasan
(74) *Attorney, Agent, or Firm* — Patterson Thuente Pedersen, P.A.

(57) ABSTRACT

A fundus camera for the recording of high-resolution color images of the fundus of non-dark-adapted eyes, and without the use of a mydriatic. The fundus camera has a strip-shaped pupil division, and includes a coherent or incoherent illumination source with illumination optics, a deflection mirror and an ophthalmoscope lens for illuminating the eye, detection optics and a detector for detecting the light reflected by the eye, and a control and evaluation unit. The deflection mirror has a strip shape, and the spatially resolving detector can be activated and read out in sectors. The control and evaluation unit connects the data read out in sectors in the form of a bright image from the detector and produce a resulting fundus image. The fundus camera records images of the fundus when the eyes are not dark-adapted for this purpose and no mydriatic has been used.

13 Claims, 4 Drawing Sheets

(56) References Cited

U.S. PATENT DOCUMENTS

| | | |
|---|---|---|
| 2004/0207811 A1 | 10/2004 | Elsner |
| 2007/0222945 A1 | 9/2007 | Tsukada et al. |
| 2009/0244482 A1 | 10/2009 | Elsner et al. |
| 2010/0123871 A1 | 5/2010 | Iwanaga et al. |
| 2010/0128221 A1 | 5/2010 | Muller et al. |

FOREIGN PATENT DOCUMENTS

| | | |
|---|---|---|
| WO | WO 99/27843 A1 | 6/1999 |
| WO | WO 00/21432 A1 | 4/2000 |

* cited by examiner

FUNDUS CAMERA WITH STRIP-SHAPED PUPIL DIVISION, AND METHOD FOR RECORDING ARTIFACT-FREE, HIGH-RESOLUTION FUNDUS IMAGES

RELATED APPLICATIONS

The present application is a National Phase entry of PCT Application No. PCT/EP2011/005558, filed Nov. 4, 2011, which claims priority from DE Application No. 10 2010 050 693.1, filed Nov. 6, 2010, which applications are hereby incorporated by reference herein in their entirety.

FIELD OF THE INVENTION

The present invention relates to a fundus camera, having strip-shaped pupil division, for recording high-resolution color images of the fundus of non-dark-adapted eyes, and without the use of mydriatic drops.

BACKGROUND

The fundus cameras known from the prior art, by means of which artifacts of undesirable eye interfaces may be suppressed, may be divided into basically three optical device classes.

Classical wide-field fundus cameras which use annular pupil division as the most important feature may be included in the first group. While the ocular fundus is illuminated by an external illumination ring, the light that is scattered back from the fundus is detected through the circular center zone of the pupil of the eye, which is free of illumination light. To delimit the external illumination ring from the detection area in the center of the pupil of the eye, a transition zone approximately 1 mm wide in which neither illumination nor detection occurs is present between the two areas. This transition zone is necessary to achieve a complete separation of illumination beams and detection beams, not only in the corneal plane, but also in the entire anterior chamber of the eye, i.e., from the posterior side of the cornea to the anterior side of the lens of the eye. Although wide-field fundus cameras may be used to record reflection-free images of the ocular fundus due to the distinct separation of illumination and detection, the achievable fundus angle is limited by the annular pupil division, and reaches maximum values of approximately 45 degrees for pupil diameters of approximately 4-5 mm. Pupil diameters of 2 mm, which occur in non-dark-adapted eyes, are not possible.

A second group of fundus imaging devices includes ophthalmoscopes, of which primarily confocal scanning laser ophthalmoscopes (CSLO) and line-scanning laser ophthalmoscopes (LSLO) have become established. In a scanning laser ophthalmoscope, the ocular fundus is scanned by a focused laser beam, and the light scattered back from the retina is imaged through a detection aperture onto an image sensor. Due to the confocal detection, reflections and scattered light from various planes of the eye, for example from the cornea or the lens of the eye, are suppressed, and artifact-free images of the ocular fundus may be recorded.

Since line-scanning laser ophthalmoscopes (LSLOs) have a design similar to that of CSLOs, the properties of the latter correspondingly apply. In contrast to CSLOs, in LSLOs the ocular fundus is scanned by use of a laser line instead of a laser spot. However, the suppression of interference signals is generally not as good as in CSLOs. In return, LSLOs are less technically complex, less expensive, and easier to adjust to the eye to be examined.

However, if the CSLO is not optimally aligned with the eye to be examined, or if the eye to be measured differs from an average eye for which the CSLO has been optimized, during the suppression of the undesirable scattered light, portions of the light scattered back from the retina and intended for detection are also suppressed. For this reason, the CSLOs, which are generally quite expensive, are used primarily as "high end" devices which allow very high-quality fundus recordings, but which are much more difficult to adjust to the eye to be measured compared to, for example, the wide-field fundus cameras mentioned in the first group.

Another disadvantage of scanning laser ophthalmoscopes is that recording a color fundus image by the scanning process takes considerably longer than for wide-field systems. The motion artifacts which result, in particular in restless patients, additionally complicate and/or impair the recordings. Another limitation in the use of CSLOs is their high level of technical complexity and the resulting higher acquisition costs, for which reason they are seldom used in the "low end" sector.

The third group includes wide-field fundus cameras having transscleral illumination. In these fundus cameras, the retina is imaged on a camera sensor, utilizing the entire pupil of the eye. The illumination occurs through the sclera of the eye. A complete separation of the illumination beam path and the detection beam path may be ensured in this way. Despite these major advantages, fundus cameras having transscleral illumination have not become established on the market since their development by Pomeratzeff (1974).

To achieve an artifact-free image, in these fundus cameras an illumination optical fiber is placed directly on the sclera (in the area of the pars plana). Significant application-related limitations result from this direct contact between the illumination optical fiber and the eye. Thus, the illumination optical fiber must, for example, be cleaned and sterilized before each diagnosis.

Each of these three groups of fundus imaging devices has specific advantages as well as disadvantages, but none is able to meet all required specifications.

SUMMARY OF THE INVENTION

The present invention includes a specialized type of illumination for a fundus camera, by application of which it is possible to record high-resolution color fundus images without visible artifacts. The fundus camera is able to image a fundus angle of 45° in the absence of mydriatic drops and for non-dark-adapted eyes, i.e., for a pupil diameter of approximately 2 mm. To reliably exclude possible contact with the eye during adjustment of the fundus camera, the fundus camera or its boundary facing the eye is situated at a distance less than approximately 10-20 mm from the eye. Despite low manufacturing costs, a simple design, and problem-free adjustability to the eye to be examined, the fundus camera achieves resolutions of 60 lp/mm in the center of the image field.

A fundus camera according to an embodiment of the invention has a strip-shaped pupil division, and includes an illumination source having illumination optics, a deflecting mirror, and an ophthalmoscope lens for illuminating the eye, detection optics and a detector for imaging the light reflected from the eye, as well as a control and evaluation unit. An incoherent illumination source is present, the deflecting mirror has a strip shape, the detector has a spatially resolving characteristic and is activatable and readable sector by sector, and the control and evaluation unit is able to link the data, read out sector by sector from the detector, in the form of a bright image to produce a resulting fundus image.

In the method according to the invention, based on a fundus camera having strip-shaped pupil division, for recording artifact-free, high-resolution images, the eye is illuminated by an illumination source via illumination optics, a deflecting mirror, and an ophthalmoscope lens, and the light reflected from the eye is imaged, via the ophthalmoscope lens and detection optics, on a detector and read out, recorded, and evaluated by a central control and evaluation unit. The illumination source emits incoherent radiation which is limited to a slit shape and is guided over the ocular fundus in a scanning manner. The light reflected from the eye, as an image of the slit, strikes corresponding sectors of a spatially resolving detector, and is read out sector by sector as data by the control and evaluation unit and linked to form a resulting fundus image.

The present fundus camera, according to an embodiment of the invention, having a strip-shaped pupil division is provided for recording high-resolution color images of the fundus, wherein for this purpose the eyes are not dark-adapted, and no mydriatic drops have been used. In addition to the fundus cameras known from the prior art and described above, the proposed approach represents an alternative which may find widespread application due to its simple design and low manufacturing costs.

BRIEF DESCRIPTION OF THE DRAWINGS

The invention is described in greater detail below with reference to exemplary embodiments, as follows.

DETAILED DESCRIPTION

The fundus camera according to an embodiment of the invention having strip-shaped pupil division includes an illumination source having illumination optics, a deflecting mirror, and an ophthalmoscope lens for illuminating the eye, detection optics and a detector for imaging the light reflected from the eye, as well as a control and evaluation unit. In particular, a coherent or incoherent illumination source is present. Furthermore, the deflecting mirror has a strip shape, and the detector having a spatially resolving characteristic is activatable and readable sector by sector. For this purpose, the control and evaluation unit is able to link the data, read out sector by sector from the detector, in the form of a bright image to produce a resulting fundus image.

Figure 1:
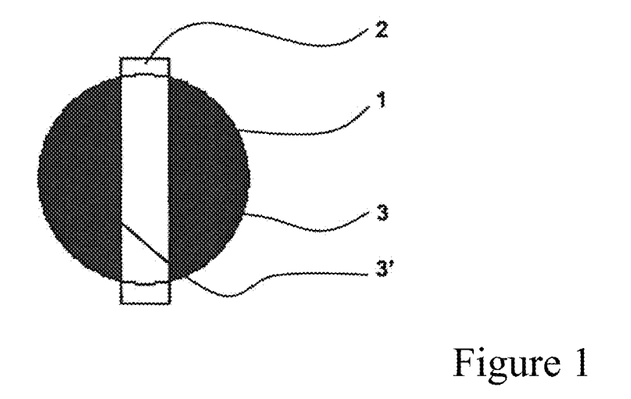
FIG. 1: is a schematic diagram concerning strip-shaped pupil division.

In this regard, FIG. 1 is a schematic diagram concerning strip-shaped pupil division of the eye to be examined. The light vertical bar denotes the illumination zone 2, while the two gray circular segments 3 and 3' represent the detection zones in the pupil 1.

The first example embodiments relate to the incoherent illumination source in the form of a wide-field light source. LEDs are particularly preferably used in addition to halogen lamps and flash lamps. In the source plane a surface is illuminated which corresponds to the range of the ocular fundus to be measured (approximately 45°-100°, for example).

The incoherent illumination source also has an additional slit aperture whose slit has a width corresponding approximately to a range of $1/5$ to $1/100$ of the fundus range to be measured and a length corresponding to the entire fundus range to be measured, and which is oriented perpendicularly with respect to the strip-shaped deflecting mirror.

To allow better adaptation of the design to different eyes and cataract thicknesses, it is advantageous to vary the width of the slit, for which purpose a motor is used, for example.

In addition, in a first design it is possible to configure the slit aperture of the illumination source in a displaceable manner for the scanning movement of the illumination radiation over the eye to be examined. This translational displacement is achieved by means of a motor, for example.

In this regard, it may be advantageous for the incoherent illumination source to include multiple wide-field light sources, and to have appropriate optical components for superimposition and homogenization of the radiation thereof.

The incoherent illumination source composed of multiple wide-field light sources represents a virtual illumination source which images the superimposed and homogenized radiation thereof into the so-called source plane. In one example variant, the light from multiple colored LEDs (for example, infrared, green, blue, and red) is collimated by aspheres, superimposed via dichroic mirrors, and imaged into the source plane of the illumination source by an additional lens. In this regard, it is particularly advantageous to use an additional beam homogenizer, whose output then forms the source plane.

The second example embodiments relate to the strip-shaped deflecting mirror, which is designed in such a way that it has a width of 0.3 to 2 mm and a length of 2 to 8 mm when imaged into the pupil plane of the eye.

For this purpose, in a second design it is possible to configure the strip-shaped deflecting mirror in a rotatable manner for the scanning movement. The strip-shaped deflecting mirror, for example, has a galvanometer drive for achieving the scanning movement. In this variant, the strip mirror meets two functions. Firstly, it cuts the illumination bundle in a strip-shaped manner, thus dividing the illumination path and detection beam path, and secondly, it scans the detection field via the illumination strip. It is possible to implement these two functionalities by use of two elements: a strip-shaped mirror or prism for dividing the illumination path and detection beam path, and a second adjacent full-surface, rotatable mirror which may be motorized, for scanning the illumination pattern in the ocular fundus. This second design represents an alternative to the translational motion of the slit aperture.

During the recording, the illumination slit is moved in a scanning manner over the fundus range to be measured. For this purpose, as previously stated, either the slit aperture situated in front of the illumination source may be moved by motor, or the angular position of the strip-shaped deflecting mirror may be changed by motor. The strip-shaped deflecting mirror and the slit aperture are oriented perpendicularly with respect to one another.

The third example embodiments relate to the spatially resolving detector, which has various designs, depending on the incoherent illumination source used. For the case that the incoherent illumination source is a white light source, a color detector is used which is likewise activatable and readable sector by sector.

In contrast, for an incoherent illumination source, which is able to emit monochromatic light sequentially, preferably in the colors "red," "green," "blue," and possibly also "IR," a monochromatic detector is used.

CMOS detectors having a resolution of greater than one megapixel are for example used as spatially resolving detectors. The CMOS detectors have the advantage that they allow a read-out process referred to as "rolling shutter." In this read-out process, the lines of the detector are made sensitive to light in succession. After the exposure period, the lines are read out in the same sequence and at the same speed. For the specialized use in the present inventive approach, the detector is activated and read out sector by sector according to the "rolling shutter" process, the sectors corresponding to the width of the illumination slit, and the movement of the illumination slit being synchronized with the read-out process. In this way, the brightness of the light scattered back from the ocular fundus may be completely recorded at optimal sensitivity and speed. If the losses in speed or sensitivity are tolerated, the entire spatially resolving detector may also be used. In this case, only the sector values from the overall image are used and evaluated.

The fourth example embodiments relate to the control and evaluation unit, which is able to link the data, read out sector by sector from the detector, in the form of a bright image to produce a resulting fundus image.

Furthermore, the control and evaluation unit is designed in such a way that, in addition to the bright image which is read out sector by sector, at least one dark image is likewise read out sector by sector with the same exposure period of the particular sectors, and used for correcting the resulting fundus image.

The dark image is recorded over the same exposure period as the bright image, the detector likewise being activated and read out sector by sector according to the "rolling shutter" process, and the movement of the illumination slit being synchronized with the read-out process.

However, the so-called dark image recorded for each bright image contains no signals from the retina, but, rather, only the interfering reflections which necessarily result from the optical system and the eye and which are also contained in the bright image. These interfering reflections may be further significantly reduced in the resulting fundus image by subtracting the dark image from the bright image. The dark image may also be preprocessed, using algorithms known from the prior art, such as for smoothing and filtering, before it is subtracted from the bright image.

A technical alternative is possible using the latest generation of CMOS sensors. These sensors provide the option of a multiple region-of-interest (ROI) scan. In this regard, two sectors of the camera are read out simultaneously, so that it is possible to record the bright image and the dark image in one scanning pass, thus allowing the measuring time to be greatly reduced.

Figure 2:
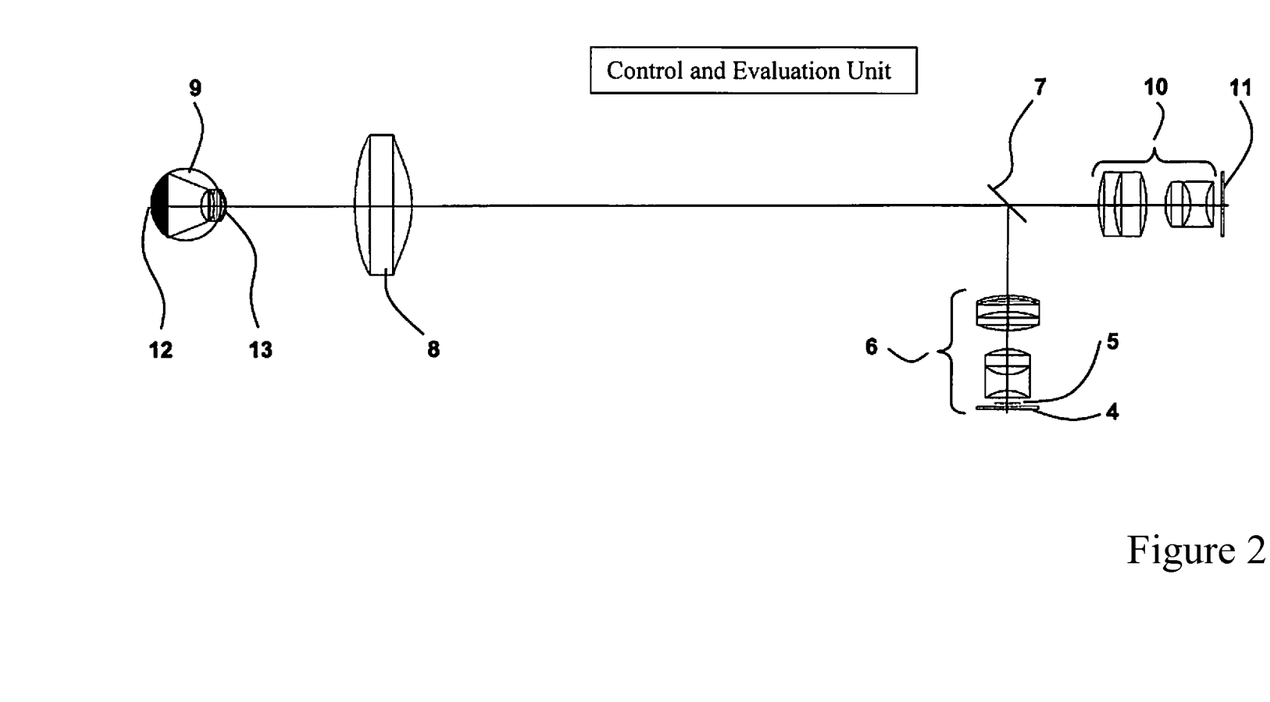
FIG. 2: depicts the schematic design of the fundus camera having pupil division.

FIG. 2 shows the schematic design of the fundus camera according to the invention, having pupil division. The fundus camera includes an incoherent illumination source 4 having a slit aperture 5 and illumination optics 6, a strip-shaped deflecting mirror 7, and an ophthalmoscope lens 8 for illuminating the eye 9, detection optics 10 and a spatially resolving detector 11 for imaging the light reflected from the eye 9, as well as a control and evaluation unit.

The system is configured in such a way that the incoherent illumination source 4, the ocular fundus 12, and the spatially resolving detector 11 are situated in conjugate planes. This likewise applies to the mirror plane of the strip-shaped deflecting mirror 7 and the anterior side of the cornea 13 of the eye 9.

In one particularly advantageous embodiment, for concentric pupil division the fundus camera according to the invention additionally has ring illumination, an aperture mirror, and a further detector, the strip-shaped deflecting mirror being designed in such a way that it may be moved into the opening in the aperture mirror. The movement may be carried out in a linear or circular manner by mechanical, electrical, magnetic, or other means.

Another embodiment provides that only one illumination unit, which has appropriate devices for producing ring illumination and slit illumination, is present, in addition at least one shutter being present which prevents the ring illumination as well as slit illumination from being active.

Figure 4A:
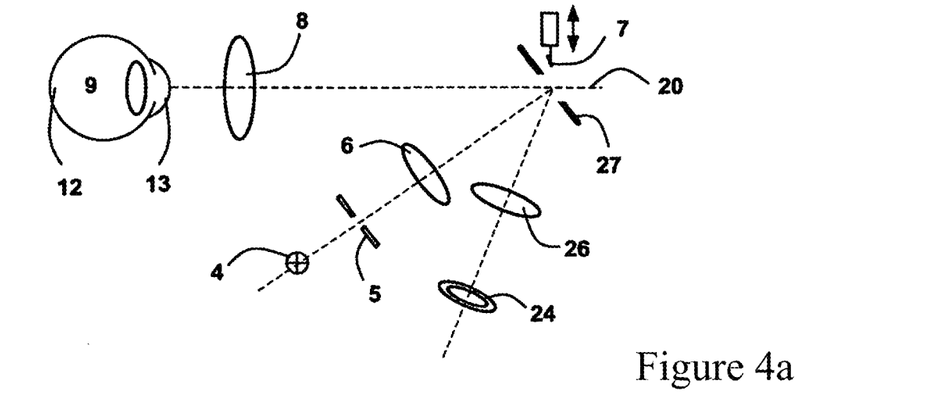
FIG. 4a: depicts the schematic design of a fundus camera having strip-shaped pupil division and concentric pupil division, with two illumination units.
Figure 4B:
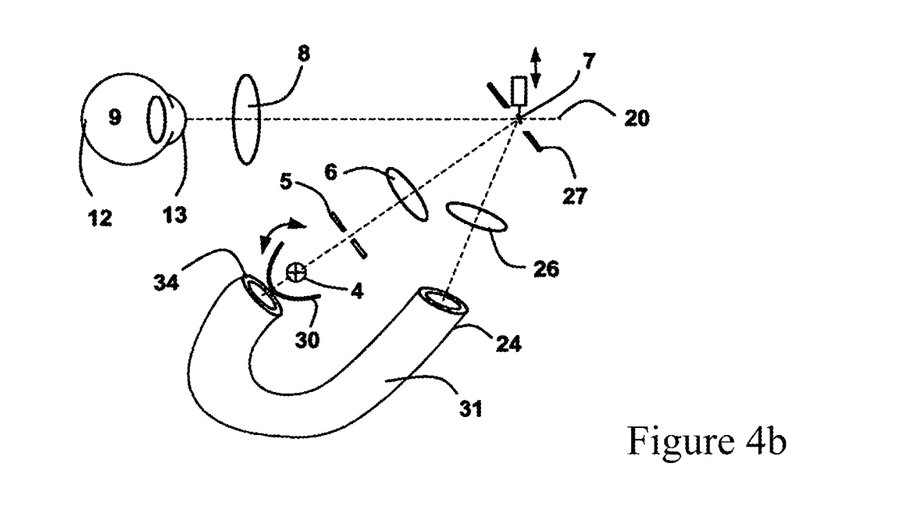
FIG. 4b: depicts the schematic design of a fundus camera having strip-shaped pupil division and concentric pupil division, with only one illumination unit.

In this regard, FIGS. 4a and 4b show schematic illustrations of the illumination beam paths of the fundus camera according to the invention, having strip-shaped pupil division and concentric pupil division.

The fundus camera in FIG. 4a has separate illumination units, while FIG. 4b shows a fundus camera having only one illumination unit, which is suitable for illumination for strip-shaped pupil division as well as for concentric pupil division.

According to FIG. 4a, a fundus camera having concentric pupil division is used to record images of the eye 9. For this purpose, the strip-shaped deflecting mirror 7 is retracted from the beam path 20, in particular from the opening in the aperture mirror 27. The illumination of the eye 9 is carried out, starting from the ring illumination 24, via the illumination optics 26 and the aperture mirror 27, the light source 4 being inactive.

In contrast, according to FIG. 4b a fundus camera having strip-shaped pupil division is used to record images of the eye 9. For this purpose, the strip-shaped deflecting mirror 7 is advanced into the beam path 20, in particular into the opening in the aperture mirror 27. The illumination of the eye 9 is carried out, starting from the light source 4, via the slit aperture 5, the illumination optics 6, and the strip-shaped mirror 7. A rotatable shutter 30 prevents light from the light source 4 from being coupled into the fiber bundle 31, and the output of the fiber bundle from being used as ring light 34.

The advantageous embodiment proposed here describes a fundus camera in which three basic types of fundus cameras are combined into a hybrid fundus camera.

Thus, classical wide-field fundus cameras, which operate according to the mydriatic or the nonmydriatic principle, have a fixed aperture mirror which determines the diameter of the observation aperture and the diameter of the illumination ring. Mydriatic fundus cameras, in which the pupil of the eye is dilated for the examination using certain pharmaceuticals, offer the advantage of a large observation aperture and associated high sensitivity with good image quality. In contrast, examinations using nonmydriatic fundus cameras may be carried out even for pupil diameters of approximately 3 mm; as the result of the small observation aperture, however, lower sensitivity with reduced image quality is to be expected. A combination of the advantages of both principles is possible only with a significant level of technical complexity and reduced image quality.

In addition, it should be noted that very small pupils of patients (<3 mm) can no longer be illuminated free of reflections using a classical wide-field fundus camera, having an annular geometrically divided pupil and image angles ≥30°.

According to the example embodiment proposed here, a mydriatic fundus camera having antireflective points and an observation aperture of at least 2.3 mm in diameter, an inner diameter of the illumination ring of at least 4.5 mm, and an inner diameter of the aperture mirror of at least 6.5 mm (values in the pupil of the eye) is supplemented by a wide-line scanner having a strip-shaped deflecting mirror which is refracted from or advanced into, or pivoted from or into, the opening in the aperture mirror, the wide-line scanner having a separate illumination beam path.

Figure 5:
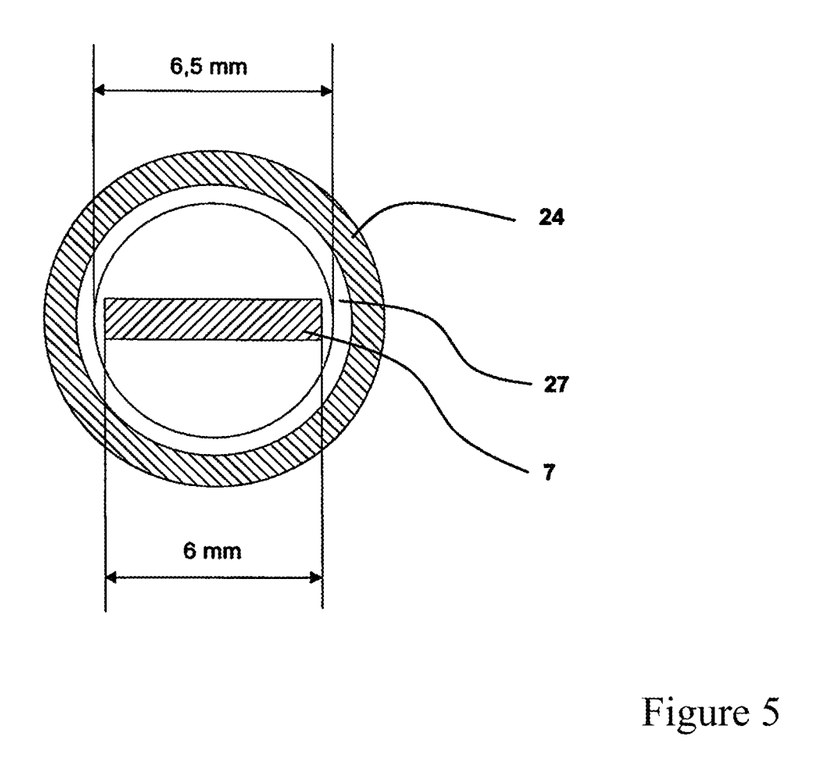
FIG. 5: depicts one possible configuration of a fundus camera having strip-shaped pupil division and concentric pupil division.

In this regard, FIG. 5 shows a configuration of a fundus camera according to the invention having strip-shaped pupil division and concentric pupil division. The dimensions of the ring illumination 24, of the aperture mirror 27, and of the strip-shaped mirror 7 are set in relation to one another. For an inner diameter of 6.5 mm of the aperture mirror 27, the strip-shaped mirror 7 has a dimension of 6 mm, for example.

In the method according to the invention for recording artifact-free, high-resolution images using a fundus camera having strip-shaped pupil division, the eye is illuminated by an illumination source via illumination optics, a deflecting mirror, and an ophthalmoscope lens, and the light reflected from the eye is imaged, via the ophthalmoscope lens and detection optics, on a detector and is read out, recorded, and evaluated by a central control and evaluation unit. The illumination source emits coherent or incoherent radiation which is limited to a slit shape and is guided over the ocular fundus in a scanning manner. The slit illumination is designed in such a way that the resulting slit image on the detector is much wider than the resolution in the detector image to be achieved in this direction. The light reflected from the ocular fundus, as an image of the slit, strikes corresponding sectors of a spatially resolving detector, and is read out sector by sector by the control and evaluation unit and synchronized with the moving illumination pattern in such a way that a bright image and a dark image are recorded, and both images are offset with respect to one another to form a resulting fundus image.

To generate incoherent radiation, illumination sources in the form of LEDs are preferably used in addition to halogen lamps and flash lamps. In the source plane a surface is illuminated which corresponds to the range (approximately)45°-100° of the ocular fundus to be measured. In this regard, it may also be advantageous to obtain the incoherent radiation from multiple wide-field light sources by superimposing and homogenizing the radiation thereof via appropriate optical components.

In contrast to a wide-field fundus camera known from the prior art, which generally uses annular pupil division, the fundus camera described here according to FIG. 1 is based on strip-shaped pupil division, in which the light bar extending over the pupil 1 represents the illumination zone 2, and the two gray circular segments 3 and 3' represent the detection zones. For this purpose, the incoherent radiation emitted by the illumination source is delimited with priority by an additional slit aperture, and subsequently delimited by a strip-shaped deflecting mirror, on the bar of the illumination zone 2.

The slit aperture which is present for the prioritized delimitation of the incoherent radiation is dimensioned in such a way that its width corresponds approximately to a range of ⅕ to ¹⁄₁₀₀ of the fundus range to be measured and a length corresponding to the entire fundus range to be measured. To allow better adaptation of the design to different eyes and cataract thicknesses, it is advantageous to vary the width of the slit, for example, by motor.

In contrast, the strip-shaped deflecting mirror which is present for the subsequent delimitation of the incoherent radiation is dimensioned in such a way that it has a width of approximately 0.3 to 2 mm and a length of 2 to 8 mm when imaged into the pupil plane of the eye.

The strip-shaped deflecting mirror and the slit aperture are oriented perpendicularly with respect to one another. According to FIG. 2, the incoherent illumination source 4, the ocular fundus 12, and the spatially resolving detector 11 are thus situated in conjugate planes, which is also the case for the mirror plane of the strip-shaped deflecting mirror 7 and the anterior side of the cornea 13 of the eye 9. The eye 9 is thus illuminated with incoherent radiation by an illumination source 4 via a slit aperture 5, illumination optics 6, a strip-shaped deflecting mirror 7, and an ophthalmoscope lens 8. The light reflected from the eye 9 is imaged, via the ophthalmoscope lens 8 and detection optics 10, on the spatially resolving detector 11 and read out, recorded, and evaluated by a central control and evaluation unit.

The incoherent radiation which is emitted by the illumination source 4 and delimited by the slit aperture 5 and the strip-shaped deflecting mirror 7 is guided over the ocular fundus 12 in a scanning manner for the measurement. The scanning movement of the slit illumination is preferably achieved by a translational motion of the slit aperture 5 or by a rotational motion of the strip-shaped deflecting mirror 7.

The scanning movement implemented by a translational motion of the slit aperture 5 in a first embodiment of the method is preferably achieved by motor.

In the second design, which represents an alternative to the translational motion of the slit aperture, the strip-shaped deflecting mirror is moved in a scanning manner, for which purpose it has a rotatable design, and for example, has a galvanometer drive or is designed as a rotatable polygon mirror.

The light reflected from the ocular fundus, as an image of the slit, strikes corresponding sectors of a spatially resolving detector, and is read out sector by sector by the control and evaluation unit and linked to form a resulting fundus image.

The spatially resolving detector may have various designs, depending on the incoherent illumination source used. For the case that the incoherent illumination source is a white light source, a color detector is used. In contrast, for an incoherent illumination source which is able to emit monochromatic light sequentially, for example in the colors "red," "green," "blue," and possibly also "IR," a monochromatic detector is used.

CMOS detectors having a resolution of greater than one megapixel are, in an example embodiment, used as spatially resolving detectors. The CMOS detectors have the advantage that they allow a read-out process referred to as "rolling shutter." In this read-out process, the lines of the detector are made sensitive to light in succession. After the exposure period, the lines are read out in the same sequence and at the same speed. For the specialized use in the present inventive approach, the detector is activated and read out sector by sector according to the "rolling shutter" process, the sectors corresponding to the width of the illumination slit, and the movement of the illumination slit being synchronized with the read-out process. In this way, the brightness of the light scattered back from the ocular fundus may be completely recorded at optimal sensitivity and speed. If the losses in speed or sensitivity are tolerated, the entire spatially resolving detector may also be used. In this case, only the sector values from the overall image are used and evaluated.

In another method, for recording the bright image the control and evaluation unit activates the particular sector for the period of time in which the image of the slit reflected from the ocular fundus completely covers the sector.

As stated above, the detector is activated and read out sector by sector according to the "rolling shutter" process, the sectors corresponding to the width of the illumination slit, and the movement of the illumination slit being synchronized with the read-out process.

Figure 3:
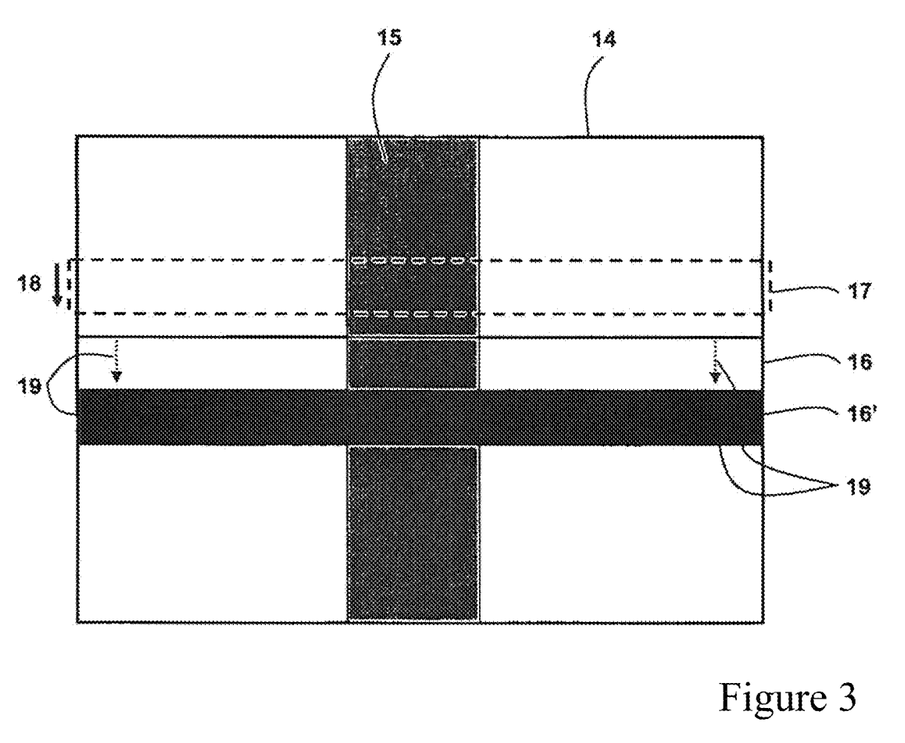
FIG. 3: is a schematic illustration of the detector surface, with the light components reflected from the eye depicted thereon.

In this regard, FIG. 3 shows a schematic illustration of the detector surface, with the light components reflected from the eye depicted thereon. The illustrated detector surface 14 corresponds to the image field on the ocular fundus to be measured. The vertical bar characterizes the corneal reflection 15 resulting from the slit illumination, while the two horizontal bars represent, by way of example, two sectors 16 and 16' of the detector surface 14 which is divided into 5 to 100 sectors. The bar illustrated in dashed lines, which for the sake of clarity projects beyond the detector surface 14, represents the image of the slit 17 reflected from the ocular fundus, the arrow indicating the direction of motion 18 of the slit 17 over the detector surface 14. Since the spatially resolving detector used preferably has a resolution of greater than one megapixel, the individual sectors contain multiple lines of the detector, which are represented by the arrows 19.

The synchronization between illumination and read-out is designed in such a way that the first (topmost) line of the sector 16 is activated as soon as the first (lower) boundary of the illumination slit 17 meets this line. This first (topmost) line of the sector 16 is not deactivated until the last (topmost) boundary of the illumination slit 17 no longer meets this line. Since for this period of illumination the control and evaluation unit also carries out the appropriate read-out, the entire image of the slit reflected from the ocular fundus is detected.

As is apparent from the schematic illustration of the detector surface according to FIG. 3, not only the image of the slit reflected from the ocular fundus, but also interfering reflections, for example in the form of the corneal reflection 15, are imaged on the detector surface 14. Therefore, in the implementation of the resulting fundus images an effort should be made to eliminate interfering reflections. The reflections from the posterior side of the cornea and the lens of the eye are considerably weaker, but have properties similar to the corneal reflection 15 illustrated in FIG. 3.

In addition to optical devices for interference light suppression, methods referred to as "structured illumination" are known which do not suppress the interference light, but instead measure it to allow the interference light to be eliminated from the recording. For this purpose, for example two recordings having inverse aperture patterns are taken, a bright image and a dark image are computed, and the difference image from the bright image and the dark image is determined as the result. The dark background to be subtracted has a certain photon noise which statistically changes between the dark image and the bright image. Thus, although the interference light in principle may be completely separated from the measuring signals, the measuring signals are superimposed by the noise of the subtracted dark signal. This effect is more apparent the stronger the relative component of the interference light which is subtracted from the recording. Both effects, the impairment of the measurement image firstly by an additive interference light component for the LSLO, and secondly, an additive interference light noise component for the "structured illumination," are physically different, and thus allow independent optimization of the two effects.

For this reason, in the method according to the invention, for each recorded bright image a second image, the so-called dark image, is recorded. The dark image contains no signals from the retina, but, rather, only interfering reflections from the optics and the eye. The dark image is subtracted from the bright image in order to further significantly reduce the interfering reflections.

To be able to eliminate interfering reflections, for example in the form of the corneal reflection 15 illustrated in FIG. 3, as completely as possible from the resulting fundus images, it is important that the interfering reflections which superimpose the bright image, and the interfering reflections which are measured in the dark image, have intensity distributions that are as similar as possible. This is not automatically the case, particularly when the interfering reflections in the image change quickly from a spatial standpoint.

For recording a dark image, it is important that the control and evaluation unit activates the particular sector for the same period of time in which the image of the slit reflected from the ocular fundus has completely covered the sector. The dark image is therefore recorded with the same exposure period as the bright image, and is likewise synchronized with the rolling shutter. The dark image may be recorded before and also after the bright image. Two dark images may also be recorded before and after the bright image, offset with respect to one another in the evaluation unit, and then subtracted from the bright image.

According to FIG. 3, for the dark image the first (topmost) line of the sector 16' is activated as soon as the first (lower) boundary of the illumination slit 17 meets the first (topmost) line of the sector 16. This first (topmost) line of the sector 16' is not deactivated until the last (topmost) boundary of the illumination slit 17 no longer meets the first (topmost) line of the sector 16. Since the slit 17 moves from top to bottom over the detector surface 14 corresponding to the direction of motion 18, the dark image for the sector 16' is recorded before the corresponding bright image.

In principle, however, it is also possible to record more than one dark image, the images being appropriately averaged. The dark images may be recorded before and/or after the bright image is recorded.

To be able to achieve high-resolution color recordings of the fundus using the method according to the invention, in principle the following two variants may be implemented:

If the eye is illuminated with white light by the incoherent illumination source, a color detector must be used. In contrast, for sequential monochromatic illumination of the eye, for example with light of the colors "red," "green," and "blue," a monochromatic detector is required.

Also, when a spatially resolving color detector is used, the light reflected from the ocular fundus, as an image of the slit, is imaged onto corresponding sectors of a spatially resolving detector, read out sector by sector by the control and evaluation unit, and linked to form a resulting fundus image. Also, when illumination is carried out using incoherent white light, in addition to the bright image at least one dark image is recorded and used for correcting the resulting fundus image.

However, the eye is preferably illuminated sequentially by the incoherent illumination source using monochromatic light, preferably in the colors "red," "green," "blue," and "IR," so that a spatially resolving monochromatic detector generally is used. A resulting color fundus image is determined from the sequential color images of the ocular fundus. Here as well, in addition to the bright image at least one dark image is recorded and used for correcting the resulting fundus image.

Sequential color recordings, having slightly greater technical complexity, have the advantage that they allow more sensitive measurements, and reduce color errors by synchronous refocusing of the illumination optics and of the detection optics. In addition, sequential color recordings provide higher resolutions and better color contrast, since color interpolations may be dispensed with.

Sequential color recordings offer the further advantage that the number of dark images to be implemented may be reduced. Thus, it is possible, for example, that in addition to the monochromatic bright images, for example, in the colors "red," "green," and "blue," only one dark image is recorded. In this regard, for each color, in addition to a bright image only one-third of a dark image is recorded and linked to form a complete dark image. The overall recording process may thus be significantly speeded up.

Another embodiment of the method provides that for recording images a fundus camera is used, by use of which the eye is illuminated by an illumination source via illumination optics, a deflecting mirror, and an ophthalmoscope lens, and the light reflected from the eye is imaged, via the ophthalmoscope lens and detection optics, on a detector and read out, recorded, and evaluated by a central control and evaluation unit, for this purpose strip-shaped division or concentric pupil division being selected.

When strip-shaped pupil division is selected, this is achieved in that the illumination source which is limited to a slit shape is activated and guided over the ocular fundus in a scanning manner with the aid of the strip-shaped deflecting mirror, which for this purpose is moved into the opening in the aperture mirror that is present. The light reflected from the eye, as an image of the slit, strikes corresponding sectors of a spatially resolving detector, the data of which are read out sector by sector by the control and evaluation unit and linked to form a resulting fundus image.

When concentric pupil division is selected, the ring illumination is activated and the ocular fundus is illuminated via the aperture mirror. The light reflected from the eye then passes through the opening in the aperture mirror and strikes a detector, the data of which are read out by the control and evaluation unit and linked to form a resulting fundus image.

The present approach provides very good interference light suppression, since on the one hand the interference light components are to be confocally suppressed, and on the other hand the nonsuppressed residual interference light components in the form of a dark image are measured and subtracted from the bright image.

By the use of a wide illumination slit which is much wider (10-100 times) than the resolution to be achieved, the method provides a greatly increased (10-100 times) light guidance factor compared to LSLO, and thus allows the use of incoherent light sources. In addition, the method provides greatly improved interference light suppression due to the recording and subtraction of a dark image.

For certain highly specific details of the fundus tissue to be diagnosed, this greatly improved interference light/scattered light suppression and the associated increase in signal efficiency is extremely important. If, for example, autofluorescence recordings of the ocular fundus are prepared, the fluorophores present in the fundus tissue re-emit only very low fluorescent light intensities, which may still also be superimposed by interference light components from the lens of the eye. In such cases, the illumination may also be carried out using coherent sources. However, as a result of the described method having illumination of a wide slit (much wider than the resolution to be achieved in this direction), the recording of a bright image and a dark image, and the offsetting of the two images with respect to one another to form a resulting fundus image, in this case the method may be clearly differentiated from a classical line scanner, in which on the one hand the resolution and the illuminated slit width always substantially match, and on the other hand no dark image correction is carried out. Due to these two modifications, the effective illumination time achieved at a fundus point may be increased and may thus be decoupled from the image recording time, thus allowing significantly increased recording sensitivity, in particular for a limitation of the illumination intensity by the laser standard 60825. The second important advantage of the method is the more specific detection of fluorescence signals from the focal plane of the detection system as a result of subtracting the dark image.

The approach according to the invention provides a fundus camera and a method for recording fundus images, by application of which it is possible to record high-resolution color fundus images without visible artifacts. The fundus camera may image a fundus angle of 45° for non-dark-adapted eyes, i.e., for a pupil diameter of approximately 2 mm.

Possible contact with the eye while adjusting the fundus camera may be essentially ruled out. The fundus camera according to the invention is characterized by a simple design with low manufacturing costs. In addition, problem-free adjustability to the eye to be examined may be ensured, even for inexpert medical practitioners and for critical patients. As a result, patient assistance may be completely dispensed with.

The invention claimed is:

1. A method for recording images using a fundus camera having a strip-shaped pupil division, comprising:
    illuminating the eye by an illumination source via illumination optics, a deflecting mirror, and an ophthalmoscope lens;
    imaging light reflected from the eye, via the ophthalmoscope lens and detection optics, on a detector;
    reading out, recording, and evaluating imaging light reflected from the eye by a central control and evaluation unit;
    scanning coherent or incoherent radiation emitted from the illumination source which is limited to a slit shape over the ocular fundus;
    structuring the illumination slit such that the resulting slit image on the detector is much wider than the resolution in the detector image to be achieved in a direction of the slit image, wherein the light reflected from the eye, as an image of the slit, strikes corresponding sectors of a spatially resolving detector; and
    reading out the data with the control and evaluation unit from the detector sector by sector and synchronizing with the moving illumination pattern in such a way that a bright image and a dark image are recorded, and both images are offset with respect to one another to form a resulting fundus image.

2. The method according to claim 1, further comprising delimiting the incoherent radiation of the illumination source with priority by an additional slit aperture, and subsequently delimiting the incoherent radiation of the illumination source by making the deflecting mirror a strip-shaped deflecting mirror.

3. The method according to claim 2, further comprising varying the width of the slit aperture.

4. The method according to claim 3, further comprising using a motor to vary the width of the slit aperture.

5. The method according to at claim 1, further comprising achieving the scanning movement of the slit illumination by a rotational motion of the deflecting mirror or by a translational motion of the slit aperture.

6. The method according to claim 5, further comprising, for recording the bright image, activating via the control and evaluation unit, the particular sector for the period of time in which the image of the slit reflected from the ocular fundus completely covers the sector.

7. The method according to claim 1, further comprising, for recording at least one dark image, activating via the control and evaluation unit, the particular sector for the same period of time in which the image of the slit reflected from the ocular fundus has completely covered the sector, the dark image being used for correcting the resulting fundus image.

8. The method according to claim 7, further comprising recording the dark image or image before and/or after the bright image is recorded and appropriately averaging multiple dark images.

9. The method according to claim 1, further comprising using a spatially resolving color detector when the incoherent illumination source emits white light, and recording at least one dark image in addition to the bright image.

10. The method according to claim 1, further comprising using a spatially resolving monochromatic detector when the incoherent illumination source emits monochromatic light sequentially, whereby for each color a bright image and at least one dark image are recorded.

11. The method according to claim 10, further comprising emitting the monochromatic light in the colors "red," "green," "blue," and "IR."

12. The method according to claim 1, further comprising using a spatially resolving monochromatic detector when the incoherent illumination source emits monochromatic light sequentially.

13. The method according to claim 12, wherein the incoherent illumination source emits monochromatic light sequentially in the colors "red," "green," and "blue," and further comprising recording, for each color, in addition to a bright image only one-third of the dark image and linking the one third dark images to form a complete dark image.

* * * * *